United States Patent [19]

Cooper et al.

[11] Patent Number: 5,264,540
[45] Date of Patent: Nov. 23, 1993

[54] AROMATIC POLYANHYDRIDES

[75] Inventors: Kevin Cooper, Bridgewater; David Wasserman, Springfield; Angelo G. Scopelianos, Whitehouse Station; Dennis D. Jamiolkowski, Long Valley, all of N.J.

[73] Assignee: Ethicon, Inc., Somerville, N.J.

[21] Appl. No.: 916,919

[22] Filed: Jul. 20, 1992

[51] Int. Cl.$^5$ ............... C08G 63/00; C08G 63/02; C08G 67/00; C08G 69/00
[52] U.S. Cl. ............... 528/272; 528/271
[58] Field of Search ............... 528/271, 272

[56] References Cited

U.S. PATENT DOCUMENTS

| | | |
|---|---|---|
| 2,849,483 | 8/1958 | Ham . |
| 2,949,483 | 8/1960 | Ham . |
| 4,414,381 | 11/1983 | Griffin et al. ............... 528/190 |
| 4,435,590 | 3/1984 | Shalaby et al. ............... 560/61 |
| 4,510,295 | 4/1985 | Bezwada et al. ............... 525/437 |
| 4,546,152 | 10/1985 | Koelmel et al. ............... 525/437 |
| 4,757,128 | 7/1988 | Domb et al. ............... 528/271 |
| 4,789,724 | 12/1988 | Domb et al. ............... 528/176 |
| 4,857,311 | 8/1989 | Domb et al. ............... 424/78 |
| 4,888,176 | 12/1989 | Langer et al. . |

OTHER PUBLICATIONS

Domb, Macromolecules, 25, 12 (1992).
Domb, et al., J. of Polymer Sci., 215 3373 (1987).
J. Am. Chem. Sco., 54, 1569 (1932).
J. Polym. Sci., 29, 343 (1958).

Primary Examiner—John Kight, III
Assistant Examiner—T. Mosley
Attorney, Agent, or Firm—Matthew S. Goodwin

[57] ABSTRACT

An improved process for preparing an aromatic polyanhydride is disclosed. The aromatic polyanhydride is prepared by reacting an aromatic dicarboxylic acid with an anhydride to form an anhydride prepolymer, isolating and purifying the prepolymer, and subjecting the prepolymer to melt polycondensation conditions. The improvement specifically relates to the purification of the acid so it is essentially free of impurities before it is reacted with the anhydride.

The polymers prepared from the improved process have higher molecular weights than the molecular weights achieved from the prior art processes, and exhibit outstanding thermal stability and mechanical properties. This combination of properties allows the aromatic polyanhydrides to be melt processed to prepare numerous devices. In addition, these aromatic polyanhydrides are bioabsorbable, and this attribute in combination with its ability for melt processing makes the polyanhydrides particularly well-suited for the preparation of implantable surgical devices such as wound closure devices which are designed to absorb in the body when exposed to moist bodily tissue.

23 Claims, 5 Drawing Sheets

AROMATIC POLYANHYDRIDES

BACKGROUND OF THE INVENTION

This invention relates to polymers of anhydrides. More specifically, it relates to aromatic polyanhydrides particularly well suited for melt processing to prepare biomedical devices, especially wound closure devices.

Polymers of aliphatic and aromatic anhydrides have been extensively studied for many years. As long ago as the 1930's, Carothers had prepared a series of aliphatic polyanhydrides for use as fibers in the textile industry (see J. Am. Chem. Soc., 54, 1569 (1932)). Later, in the mid 1950's, Conix was able to synthesize aromatic polyanhydrides with improved film and fiber forming properties (see J. Polym. Sci., 29 343 (1958)). However, these early attempts to make polyanhydrides with outstanding properties were unsuccessful because these polyanhydrides exhibited poor thermal and hydrolytic stability. Therefore, during this time, no commercial applications of polyanhydrides were found.

More recently, major advances in the preparation of polyanhydrides with sustained drug release properties have been made. U.S. Pat. Nos. 4,757,128, and Domb et al., J. of Polymer Sci., 25, 3373 (1987), disclose the preparation of polyanhydrides from pure, isolated prepolymers of diacids and acetic acid under well defined polymerization reaction conditions of temperature and time, optionally in the presence of a coordination catalyst. The molecular weight of the polyanhydrides prepared from the isolated prepolymers is reported to be higher than that achieved when an unisolated prepolymer mixture is used. However, as stated by Domb et al., the polyanhydrides depolymerize to form a rubbery gel if the polymerization temperature is maintained at elevated temperatures for an extended period of time.

The synthesis techniques described by Domb have lead to the use of polyanhydrides as biodegradable matrices for the controlled release of biologically active substances. See, for example, U.S. Pat. No. 4,857,311, and U.S. Pat. No. 4,888,176. One of the factors which make a polyanhydride particularly well suited as a biodegradable matrix is that it breaks down into biocompatible degradation products based on the monomeric diacids when exposed to moist bodily tissue for extended periods of time. These biocompatible degradation products can be readily passed through the tissue without any significant tissue response or harm to the digestive or vascular systems.

Recent attempts have been made to optimize the synthesis of anhydride copolymers. Specifically, anhydride copolymers which will exhibit longer release and degradation times when used as a matrix for drug release have been studied. U.S. Pat. No. 4,789,724 describes preparing copolymers from individually prepared, isolated prepolymers. Domb, Macromolecules, 25, 12 (1992), describes preparing relatively low molecular weight (I.V. <0.45 dl/g) aromatic copolymers of anhydrides which are highly soluble in conventional solvents, and therefore suitable for the preparation of solvent cast drug release devices. Although the extensive studies performed by Domb and his colleagues, as described above, have shown the feasibility of preparing certain polyanhydrides which are suitable as matrices for drug release, this significant class of polyanhydrides are unsuitable for numerous biomedical applications, especially for the preparation of implantable devices for wound closure. Upon a careful review of Domb's work, it becomes apparent that Domb was able to prepare aliphatic polyanhydrides of high molecular weight, but the reported values for the molecular weight of polyanhydrides which are predominately aromatic are too low for conventional melt processing techniques required to make biomedical devices. Although it is possible to prepare drug delivery devices from aliphatic polyanhydrides, it is most likely that it would not be possible to make biomedical devices from the aliphatic polyanhydrides described in Domb due to their poor thermal stability. However, it would be highly desirable to fabricate devices from polymers which can withstand the effects of melt processing and sterilization using conventional melt processing and irradiation techniques. In this regard, the incorporation of aromatic functionality in the polymer chains of the polyanhydride is critical for the application of melt processing to fabricate biomedical devices or the application of irradiation to achieve sterilization. See, for example, U.S. Pat. Nos. 4,435,590, 4,510,295, and 4,546,152, which describe the preparation of polymers for biomedical applications with a high degree of aromatic functionality capable of withstanding the effects of irradiation for sterilization.

Other polymer compositions containing anhydride functionality have been described in the literature. For example, U.S. Pat. No. 4,414,381 describes the preparation of poly(ester-anhydride) copolymers. These copolymers are described as being melt processable, and useful for preparing fibers, films and molding powders. Unfortunately, these copolymers are not bioabsorbable, and therefore are unsuitable for numerous implantable, medical device applications.

The failure of Domb and others to synthesize bioabsorbable, aromatic polyanhydrides with high molecular weights limits the suitability of such polyanhydrides to their use as matrices for the delivery of biologically active substances. In view of this deficiency, it would be most desirable if an aromatic polyanhydride could be prepared of sufficiently high molecular weight. Accordingly, it would be desirable to prepare an aromatic polyanhydride which exhibits the requisite processing flexibility for the preparation of biomedical devices, especially using melt processing techniques such as injection or extrusion molding. Likewise, it would be desirable to prepare aromatic polyanhydrides with outstanding thermal and dimensional stability at elevated temperatures for prolonged periods, and the ability to maintain physical and biological properties upon sterilization using conventional irradiation techniques. All of these properties would be most beneficial in a bioabsorbable, aromatic polyanhydride for the preparation of biomedical devices, especially implantable wound closure devices and adhesion prevention barriers which are absorbable in bodily tissue without causing adverse tissue response or other adverse reactions.

SUMMARY OF THE INVENTION

In one aspect, the invention is an improved process for preparing an aromatic polyanhydride. In this process, a highly purified aromatic dicarboxylic acid is reacted with an anhydride to form an aromatic anhydride prepolymer. The prepolymer is isolated and purified, and subsequently the prepolymer is polymerized under melt polycondensation conditions. The improvement in the process specifically relates to the purification of the aromatic dicarboxylic acid so that the acid is essentially free of impurities before it is reacted with the anhydride.

Surprisingly, the purification of the aromatic dicarboxylic acid prior to its reaction with the anhydride provides greater flexibility when choosing the operating conditions for the melt polycondensation of the anhydride prepolymer. The polymerization can be carried out over longer time periods without the degradation previously observed, by Domb, for the aromatic polyanhydride produced. Consequently, the molecular weight of the aromatic polyanhydride, as measured by its inherent viscosity, can be significantly increased relative to the molecular weight obtained for aromatic polyanhydrides produced using the conventional methods where the aromatic dicarboxylic acid is not purified as described herein.

In addition, the greater processing flexibility inherent in the improved process allows the opportunity to vary widely the polymerization temperature under which the melt polycondensation of the prepolymer is to occur. Most notably, higher polymerization temperatures greater than about 180° C. can be maintained without fear of thermal decomposition. These higher reaction temperatures can lead to further increases in the molecular weight of the aromatic polyanhydride prepared from the improved process, which is a highly desired effect for numerous applications. Consequently, the polymer so produced can be more easily melt processed into useful medical devices.

In another aspect, the invention is an aromatic polyanhydride prepared by the improved process set forth above. Unlike the aromatic polyanhydrides of the prior art, polyanhydrides derived from the improved process exhibit outstanding thermal stability for prolonged time periods at elevated temperatures. Under such adverse conditions, as would be present during melt processing, of elevated temperature and time, the viscosity of the polymer remains substantially constant, and there is no formation of insoluble gels which would indicate undesirable branching, crosslinking or depolymerization reactions.

The aromatic polyanhydrides of this invention exhibit not only thermal stability, but also excellent baseline mechanical properties such as tensile strength, modulus and elongation. Additionally, these excellent mechanical properties can be substantially maintained for prolonged time periods when the polymer is exposed to environmental conditions similar to those experienced in the human body. Moreover, their outstanding thermal stability has made it possible to melt process the aromatic polyanhydrides of this invention. In combination with the mechanical properties of articles so produced, numerous applications of these polymers can be utilized.

Furthermore, the aromatic polyanhydrides made by the improved process are relatively stable to the effects of conventional radiation treatments. Therefore, the outstanding mechanical properties of these polymers are not sacrificed when the polymers are exposed to radiation required for sterilization of medical grade parts.

Lastly, these aromatic polyanhydrides exhibit all of these desired properties, yet maintain their bioabsorbability when exposed to bodily tissue. The overall spectrum of properties for this new class of polymers is particularly well-suited for the preparation of biomedical devices, especially implantable wound closure devices such as surgical staples, clips and sutures. Furthermore, their application as drug delivery vehicles as well as adhesion prevention barriers should also be apparent.

DETAILED DESCRIPTION OF THE INVENTION

The conventional steps of reacting an aromatic dicarboxylic acid with an anhydride to form an aromatic anhydride prepolymer, isolating and purifying the prepolymer, and polymerizing the prepolymer under melt polycondensation conditions, are described in U.S. Pat. No. 4,757,128 (the "'128 patent") and Domb et al., J. of Polymer Sci., 25, 3373 (1987), each of which is incorporated by reference herein.

For purposes of describing this invention, the purified dicarboxylic acid is "essentially free" of impurities if the amount of non-dicarboxylic or inert impurities contained in the acid is no greater than about 0.5 percent of the weight of the acid, preferably no greater than about 0.3 percent, and most preferably no greater than about 0.1 percent. If the concentration of impurities is greater than about 0.5 percent, then it may not be possible to carry out the melt polycondensation of the anhydride prepolymer under conditions sufficient to achieve an increased molecular weight which is necessary to obtain a molded article which, after melt processing, maintains excellent mechanical properties.

The purification of the acid to remove essentially all of the impurities is advantageously performed in a two step process. The first step involves removing substantially all of the salt impurities which may have formed from the preparation of the dicarboxylic acid, which is conveniently prepared from an alkali or alkaline earth metal salt of the acid. The salt free, or "ash free", diacid can be prepared by suspending the highly insoluble sodium salt from which the acid is derived in a strongly acidic aqueous solution. This procedure should be repeated until the diacid has less than about 0.3 weight percent of any salt impurities as determined using conventional weight loss techniques. A single suspension may leave anywhere from 10 to 15 percent ash remaining in the acid, so it is often necessary to repeat the suspension step one or two more times.

The second step of the purification method requires recrystallization of the salt-free acid. The recrystallization can be accomplished with, for example, N-methylpyrrolidinone (NMP) as a solvent (see U.S. Pat. No. 2,949,483). The recrystallization step should be repeated until the salt-free diacid recrystallizes to a constant melting point, and the salt-free acid is at least about 99.5 weight percent pure as determined using NMR and elemental analysis. To achieve this degree of purity, it is often necessary to perform three recrystallizations. It may also be necessary to wash the purified acid after the third recrystallization with hot, distilled water to remove the recrystallization solvent which may be bound to the acid. Finally, for convenience, it may be desirable to wash the purified acid in a final preparation step with acetone or a similar solvent for ease of drying. Alternatively, a solvent such as dimethylacetamide (DMAC) can be utilized as well without the need of removal, with distilled hot water, of the solvent which is bound to the acid. Other solvents may be potential candidates for purification of the acid, for example, those solvents described in U.S. Pat. No. 2,849,483.

In a preferred embodiment, the aromatic anhydride prepolymer is polymerized under melt polycondensation conditions at a temperature no less than about 200° C. under reduced pressure. Higher polymerization temperatures may lead to further increases in the molecular weight of the aromatic polyanhydride, which may be desirable for numerous applications. The exact reaction conditions chosen will depend on numerous factors, including the properties of the polymer desired, the viscosity of the reaction mixture, and the glass transition temperature and softening temperature of the polymer. The preferred reaction conditions of temperature, time and pressure can be readily determined by assessing these and other factors.

In another preferred embodiment of this invention, the aromatic dicarboxylic acid is reacted with an excess of the anhydride at reflux for at least 60 minutes. This relatively longer reaction period, in comparison to the reaction time period of 15 minutes described in the previous literature, is advantageously sufficient to react substantially all of the acid with the anhydride. Therefore, in this embodiment, it becomes unnecessary to attempt removing unreacted anhydride from the reaction mixture. This may be significant because the unreacted anhydride may act as an impurity when the prepolymer is polymerized under melt polycondensation conditions, causing a destabilizing effect on the molecular weight, chemical structure, and thermal stability of the aromatic polyanhydride prepared from this polymerization.

As used herein, an aromatic dicarboxylic acid is defined as any dicarboxylic acid containing aromatic functionality. This would include the aromatic dicarboxylic acids set forth in the '128 patent, as well as those referred to in the '128 patent as aromaticaliphatic dicarboxylic acids. Preferably, the aromatic dicarboxylic acid is a diacid in which each of the carboxyl groups of the diacid is attached directly to an aromatic ring. The preferred aromatic dicarboxylic acids can be represented by the following formula:

wherein n = 1-20, inclusive

Preferably, n is 1-10, inclusive, and therefore the most preferred aromatic dicarboxylic acids are 1,2-bis(-pcarboxyphenoxy)ethane; 1,4-bis(p-carboxyphenoxy)butane; and 1,6-bis(p-carboxyphenoxy)hexane.

Another preferred class of aromatic dicarboxylic acids is represented by the following formula:

wherein n = 1-20, inclusive; and
m = 0-20, inclusive.

The anhydride which is reacted with the aromatic dicarboxylic acid to form the aromatic anhydride prepolymer can be any anhydride of a carboxylic acid. Preferably, the anhydride is an anhydride of a monofunctional carboxylic acid. The most preferred anhydride is acetic anhydride.

One of the beneficial properties of the aromatic polyanhydrides made by the improved process of this invention is that the anhydride linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the aromatic dicarboxylic acid and the anhydride for the formation of the anhydride prepolymer, it is preferable that the reaction mixture does not contain a concentration of any co-reactant which would render the subsequently prepared polymer nonabsorbable. Preferably, the reaction mixture is substantially free of any such co-reactants if the resulting polymer is rendered nonabsorbable, especially any reactants which possess aromatic polyester functionalities, which are well known to be nonabsorbable.

In another embodiment, copolymers of aromatic anhydrides can be prepared by using the same improved process of this invention. In this embodiment, a mixture of aromatic anhydride prepolymers is polymerized under melt polycondensation conditions. Advantageously, each of the prepolymers is prepared individually from its purified dicarboxylic acid according to the teachings of this invention. Once each individual prepolymer is isolated and purified, the prepolymer co-reactants can be mixed and subjected to the desired conditions of temperature and time to copolymerize the prepolymer and subsequently prepare the aromatic anhydride copolymer.

Additionally, it should be apparent that block copolymers as well as blends with other absorbable or nonabsorbable polymers could be prepared.

The aromatic polyanhydrides of this invention desirably have an inherent viscosity as measured in chloroform at 25° C. of greater than about 0.6 deciliter/gram (dl/g). When the inherent viscosity of the polyanhydride is preferably no less than 1.0 dl/g, more preferably no less than 1.2 dl/g, the polymerization of the prepolymer is conducted at a temperature of at least 200° C. In addition, these polyanhydrides can exhibit a yield stress, e.g. tensile strength, greater than about 3000 psi, preferably greater than about 4500 psi. These tensile strengths can be achieved while varying the modulus and elongation of the polymer for desired applications, depending particularly on the chemical structure of the anhydride prepolymer chosen.

The polyanhydrides of this invention can be melt processed by numerous methods to prepare a vast array of useful devices. These polyanhydrides can be injection or compression molded to make implantable medical and surgical devices, especially wound closure devices. The preferred wound closure devices are surgical clips, staples and sutures.

Alternatively, the polyanhydrides can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Useful embodiments include tubes, including branched tubes, for artery, vein or intenstinal repair, nerve splicing, tendon splicing, sheets for typing up and supporting damaged surface abrasions, particularly major abrasions, or areas where the skin and underlying tissues are damaged or surgically removed.

Additionally, the polyanhydrides can be molded to form films which, when sterilized, are useful as adhesion prevention barriers. Another alternative processing technique for the polyanhydrides of this invention includes solvent casting, particularly for those applications where a drug delivery matrix is desired.

In more detail, the surgical and medical uses of the filaments, films, and molded articles of the present invention include, but are not necessarily limited to:

Knitted products, woven or non-woven, and molded products including:
 a. burn dressings
 b. hernia patches
 c. medicated dressings
 d. fascial substitutes
 e. gauze, fabric, sheet, felt or sponge for liver hemostasis
 f. gauze bandages
 g. arterial graft or substitutes
 h. bandages for skin surfaces
 i. burn dressings
 j. orthepedic pins, clamps, screws, and plates
 k. clips
 l. staples
 m. hooks, buttons, and snaps
 n. bone substitutes
 o. needles
 p. intrauterine devices
 q. draining or testing tubes or capillaries
 r. surgical instruments
 s. vascular implants or supports
 t. vertebal discs
 u. extracorporeal tubing for kidney and heart-lung machines
 v. artificial skin and others.

Figure 1:
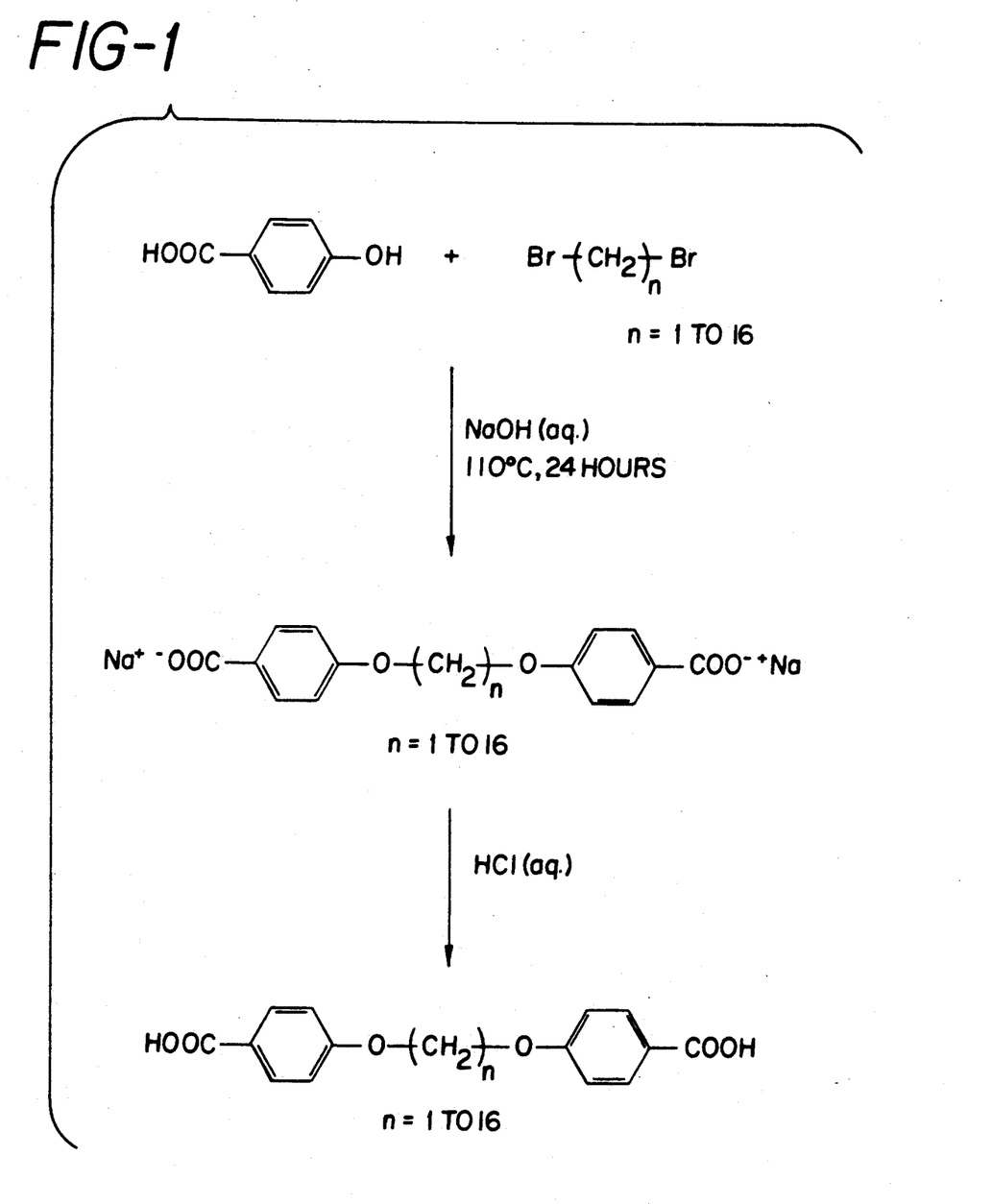
FIG. 1 illustrates a preferred synthesis for the preparation of a preferred class of aromatic dicarboxylic acids used to prepare an aromatic polyanhydride of the improved process of this invention.
Figure 2:
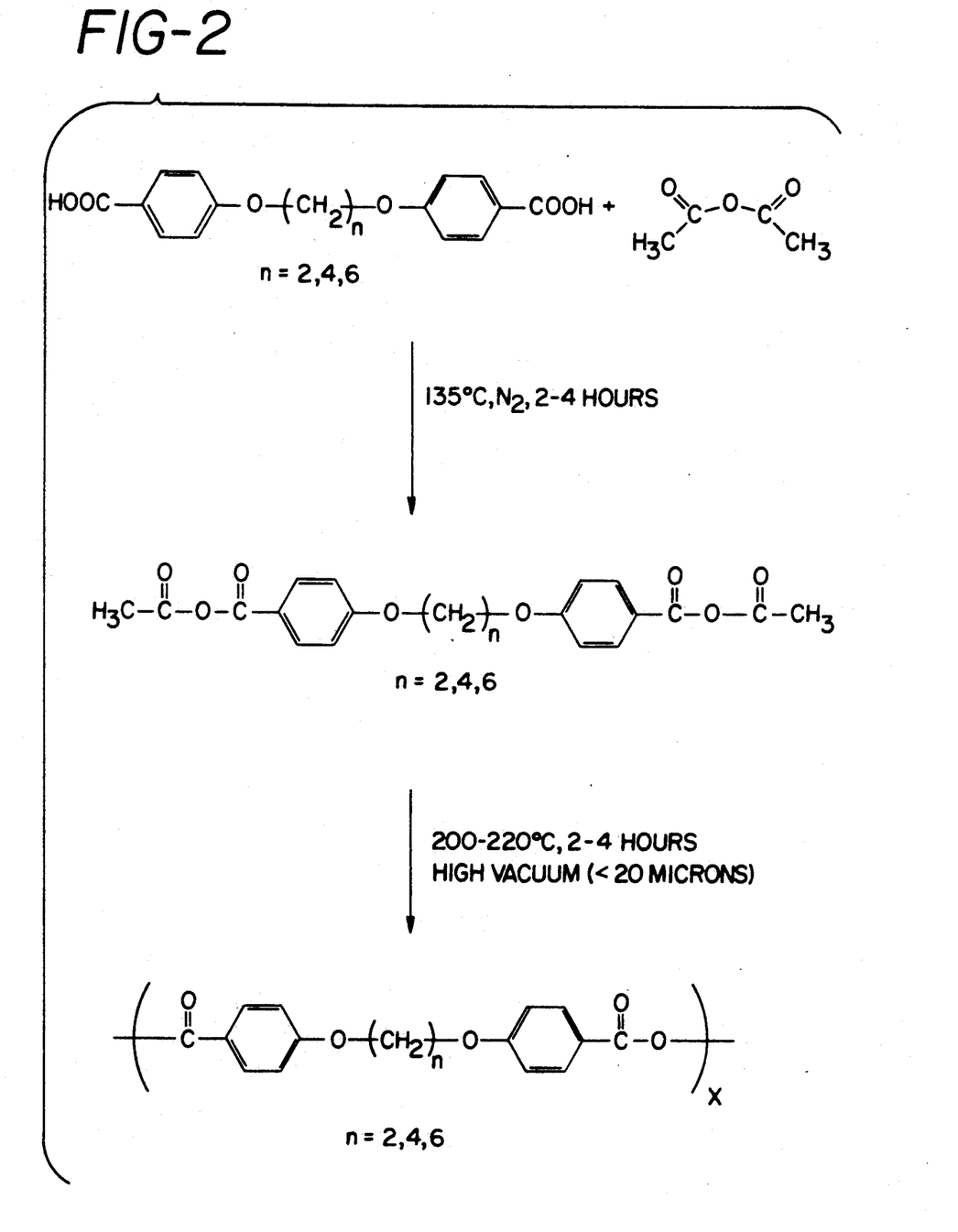
FIG. 2 illustrates a preferred synthesis for preparing a preferred class of aromatic polyanhydrides made from aromatic dicarboxylic acids made according to the synthesis shown in FIG. 1.

As an additional aid to understanding the overall process for making the aromatic polyanhydrides described herein, FIGS. 1 and 2 outline a preferred process scheme for the preparation of the preferred class of aromatic dicarboxylic acids, as well as the polyanhydrides derived from such acids.

The Examples set forth below are for illustration purposes only, and are not intended to limit the scope of the claimed invention in any way. Numerous additional embodiments within the scope and spirit of the invention will become readily apparent to those skilled in the art.

EXAMPLES

In the examples which follow, the polymers and monomers were characterized for chemical composition and purity (NMR, FT-IR, elemental analysis), thermal analysis (DSC), melt rheology (melt stability and viscosity), molecular weight (inherent viscosity), crystallinity (XRD), and baseline and in-vitro mechanical properties (Instron stress/strain).

FT-IR was performed on a Nicolet FT-IR. Polymer samples were melt pressed into thin films. Monomers were pressed into KBr pellets. $^1$H NMR was performed on a 200 MHz NMR using $CDCl_3$ as a reference. Elemental analysis was performed at Schwarzkopf Microanalytical Laboratories.

Thermal analysis of polymers and monomers was performed on a Dupont 912 Differential Scanning Calorimeter (DSC) at a heating rate of 10° C./min. A Fisher-Johns melting point apparatus was also utilized to determine melting points of monomers. Thermal gravimetric analysis was performed on a Dupont 951 TGA at a rate of 10° C./min. under a nitrogen atmosphere. Isothermal melt stability of the polymers was also determined by a Rheometrics Dynamic Analyzer RDA II for a period of i hour at temperatures ranging from 220° C. to 260° C. under a nitrogen atmosphere.

Inherent viscosities (I.V., dl/g) of the polymers were measured using a 50 bore Cannon-Ubbelhode dilution viscometer immersed in a thermostatically controlled water bath at 25° C. utilizing chloroform as the solvent at a concentration of 0.1 dl/g.

Melt viscosity was determined utilizing a Rheometrics Dynamic Analyzer RDA II at temperatures ranging from 160° C. to 290° C. at rate of 1° C./min. to 10° C./min. at frequencies of $1s^{-1}$ to $100s^{-1}$ under a nitrogen atmosphere.

Baseline and in-vitro mechanical properties of cylindrical dumbells of the poly(anhydride) polymers were performed on an Instron model 1122 at a crosshead rate of 0.35 in/min. Specimen gauge length was 0.35 in., with a width of 0.06 in. Results are an average of 8 to 12 dumbbell specimens.

The cylindrical dumbbells were prepared by utilizing a CSI Mini-max injection molder equipped with a dry nitrogen atmospheric chamber at temperatures ranging from 200° C. to 260° C. with a residence time of 3 minutes.

In-vitro studies were determined in a phosphate buffer solution (pH=7.27) at a temperature of 37° C. for periods of 1, 3, 6, and 9 weeks. Cylindrical dumbbells (8 to 10 of a total weight of 2.4 to 3.0 grams) were placed in 100 ml of buffer solution. The buffer solution was replaced on a weekly basis. Sterilization of the test articles was conducted by cobalt-60 irradiation at a dosage of 2.5 Mrad.

The filaments, fibers, were prepared, as discussed in detail in Example 3, utilizing an INSTRON Capillary Rheometer. The characteristic properties of the filaments, fibers, of the invention are readily determined by conventional test procedures. The tensile properties (i.e., straight and knot tensile strengths, Young's Modulus, and elongation) displayed herein were determined with an INSTRON tensile tester. The settings used to determine the properties mentioned above are a gauge length of 2 in., a chart speed of 10 in./min., and a crosshead speed of 2 in./min.

The straight tensile strength is calculated by dividing the force to break by the initial cross-sectional area of the fiber. The elongation at break is read directly from the stress-strain curve. Young's Modulus is calculated from the slope of the stress-strain curve of the sample in the linear elastic region.

The knot tensile strength of a fiber is determined in separate experiments. The test article is tied into a surgeon's knot with one turn of the filament around flexible tubing of ¼ inch inside diameter and 1/16 inch wall thickness. The surgeon's knot is square knot in which the free end is first passed twice, instead of once, through a loop, and the ends drawn taut so that a single knot is superimposed upon a compound knot. The first knot is started with the left end over the right end and sufficient tension is exterted to tie the knot securely. The specimen is placed in the INSTRON tensile tester with the knot approximately midway between the clamps. The knot tensile strength is calculated by dividing the force required to break by the initial cross-sectional area of the fiber.

EXAMPLE 1

Three step polymerization of 1,6-bis(acetoxycarboxyphenoxy) hexane via modified Domb and Langer method (J. Polym. Sci., 25, 3373 (1989), Macromol., 25, 12 (1992), U.S. Pat. No. 4,757,128)

The method described below is the same as Domb and Langer's method except that the monomer, 1,6-bis(p-carboxyphenoxy)hexane, was recrystallized three times from NMP.

Step 1. Synthesis of 1,6-bis(p-carboxyphenoxy)-hexane with N-methyl-pyrrolidinone (NMP) recrystallization To a nitrogen purged 5L 3-neck round bottom flask equipped with a reflux condenser, two addition funnels, and a mechanical overhead stirrer, 127.2 grams (3.2 moles of sodium hydroxide (reagent grade, Fisher) and 600 ml of distilled water were added. The vigorously stirred solution was cooled with an ice-water bath and 219.4 grams (1.6 moles of p-hydroxybenzoic acid (99%, Aldrich) was slowly added (FIG. 1).

The temperature of the homogeneous solution was then slowly raised to reflux (110° C.) via a heating mantle, and 195.18 grams (0.80 moles) of 1,6-dibromohexane (99%, Aldrich) was slowly added, dropwise, through an addition funnel over the course of 6 hours. Over the same time frame, 900 ml of distilled water was slowly added through a second addition funnel to help control the reflux temperature.

The temperature of the white slurry was then lowered below the refluxing temperature (80°-90° C.), and the reaction was allowed to continue for an additional 16 hours.

The suspended dicarboxyilc sodium salt was then cooled to 60° C. and a solution of 33 grams of sodium hydroxide in 100 ml of distilled water was slowly added through the addition funnel. The suspension was then brought to reflux (110° C.) for 15 to 30 minutes, cooled to room temperature (25° C.), and partially converted to the free dicaroxylic acid by adding one-third portions of the suspended salt to three stirring solutions of 500 ml of hydrochloric acid and 500 ml of distilled water. The stirred suspensions of partially free acid were then heated to 70° C. for 2 hours, and suction filtered through a coarse glass frit and allowed to air dry overnight.

Typically, the partially acidified (10 to 15% salt remaining after one acidification as determined by an ash test) monomer was washed one to two more times with 1500 ml of hydrochloric acid and 1500 ml of distilled water, as described above, until an ash free product was formed.

The ash free product was allowed to air dry overnight, and then was washed twice with 750 ml of acetone (99.6%, Fisher) to remove excess water and hydrochloric acid. It was then suction filtered through a Buchner funnel with a coarse glass frit and allowed to air dry overnight. The air dried monomer was then dried at room temperature under vacuum to a constant weight (3 to 4 days). The final yield was 220 grams (70%).

The white, crude 1,6-bis(p-carboxyphenoxy)hexane was then placed in a 4L Erlenmeyer flask and 1750 ml of N-methylpyrrolidinone (99+%, Aldrich) was added to yield an 8 to 1 ratio of solvent to monomer. The stirred solution was then heated to 110° C. After 1 to 2 hours, the acid monomer dissolved. The transparent, brown solution was then suction filtered to remove particulates, and allowed to stand overnight in a freezer (0° C.).

The white crystals that formed were isolated by suction filtration, and allowed to air dry for 1 to 2 hours. The partially dried monomer was then placed in a 4L Erlenmeyer flask and 1500 ml of NMP was added to yield a 7 to 1 ratio. The stirred solution was then heated to 110° C. After 1 to 2 hours the monomer dissolved, and the light brown solution was suction filtered to remove particulates. The clear solution was placed in a freezer at 0° C. and allowed to stand overnight.

The white crystals that formed were again isolated by suction filtration, and allowed to air dry for 1 to 2 hours. The partially dried monomer was recrystallized for a third time as described above, yielding a clear, light yellow solution that was allowed to stand overnight at 0° C.

The highly pure, white crystals were then isolated for a third time as described above and allowed to air dry for 2 to 3 hours. The crystals were then transferred to a 4L beaker and 1000 ml of distilled water was added (5 to 1 ratio of water to monomer). The stirred white slurry was then heated to 90° C. for 2 hours, suction filtered and washed with an additional 1000 ml of hot (90° C.) distilled water.

The monomer was allowed to air dry for 1 to 2 hours, and then was placed in a 4L beaker along with 1000 ml (5 to 1 ratio) of acetone (99.6%, Fisher), stirred for 1 to 2 hours, suction filtered, washed with an additional 1000 ml of acetone and dried under vacuum at 50° C. for 24 hours. The final yield of polymer grade 1,6-bis(p-carboxyphenoxy)hexane (99.9% pure) was 50 to 60 percent.

Step 2. Synthesis of 1,6-bis(acetoxycarboxyphenoxy)hexane

To a 5L 1-neck round bottom flask equipped with a magnetic stir bar, distillation head and water condenser, 220 grams of purified 1,6-bis(p-carboxyphenoxy)hexane and 2750 ml of acetic anhydride (99+%, Aldrich) were added to give a 12.5 to 1 ratio (ml acetic anhydride to monomer). The stirred white suspension was heated to reflux (135° C.), giving a red-brown solution free of observable particulates. The solution was concentrated by removing 1925 ml of a mixture acetic acid and acetic anhydride via the distillation head. The solution was slowly cooled to room temperature and then allowed to stand at 0° C. overnight (FIG. 2). The off-white product, 1,6-bis(acetoxycarboxyphenoxy) hexane, was isolated by suction filtration under a blanket of nitrogen and allowed to stand for 1 to 2 hours. The anhydride monomer was then transferred to a 2L Beaker and 900 ml of dry ethyl ether (reagent grade, Fisher) was added. The white slurry was stirred for 2 hours under a blanket of nitrogen, suction filtered and dried under vacuum at 50° C. for 24 hours. The final yield was 70 to 75 percent.

Step 3.
Polymerization of 1,6-bis(acetoxycarboxyphenoxy) hexane

Therefore, to a flamed-out, dry 100 ml 1-neck round bottom flask equipped with an overhead mechanical stirrer, vacuum adapter, 75° adapter, distillate bend with a vacuum takeoff and a 50 ml collection flask, 33.5 grams of freshly prepared 1,6-bis(acetoxycarboxyphenoxy)hexane was added via a nitrogen purged glove box.

The assembly was then secured to a high vacuum (<10 microns) diffusion pump and placed in a high temperature oil bath at 180° C. The stirred anhydride monomer immediately began to melt. Shortly thereafter, a high volume of distillate (acetic anhydride) began to evolve, and was collected. After 15 to 20 minutes, the viscous melt was no longer stirrable under the present reactor conditions. At such time, the polymerization was allowed to continue under high vacuum (10 to 30 microns) without stirring for a total reaction time of 120 minutes.

This first high molecular weight polymer, poly[1,6-bis(carboxyphenoxy)hexane anhydride], was removed from the bath, cooled to room temperature under a stream of nitrogen, isolated and ground. This first polymer was then placed under vacuum at 50° C. for 24 hours. The final yield was 70 to 75 percent.

A second poly[1,6-bis(carboxyphenoxy)hexane anhydride] was also prepared and isolated by the method described above, except the polymerization temperature was 200° C. The inherent viscosities of the first and second polymers are given in Table 1 and are designated as "Experiment A".

A third poly[1,6-bis(carboxyphenoxy)hexane anhydride] was also prepared and isolated by the method described above, except the polymerization temperature was 180° C. and the polymerization time was 240 minutes.

A fourth poly[1,6-bis(p-carboxyphenoxy)hexane anhydride] was also prepared and isolated by the method described above, except the polymerization temperature was 200° C. The inherent viscosities of the third and fourth polymers are given in Table 1 and are designated as "Experiment B".

Figure 3:
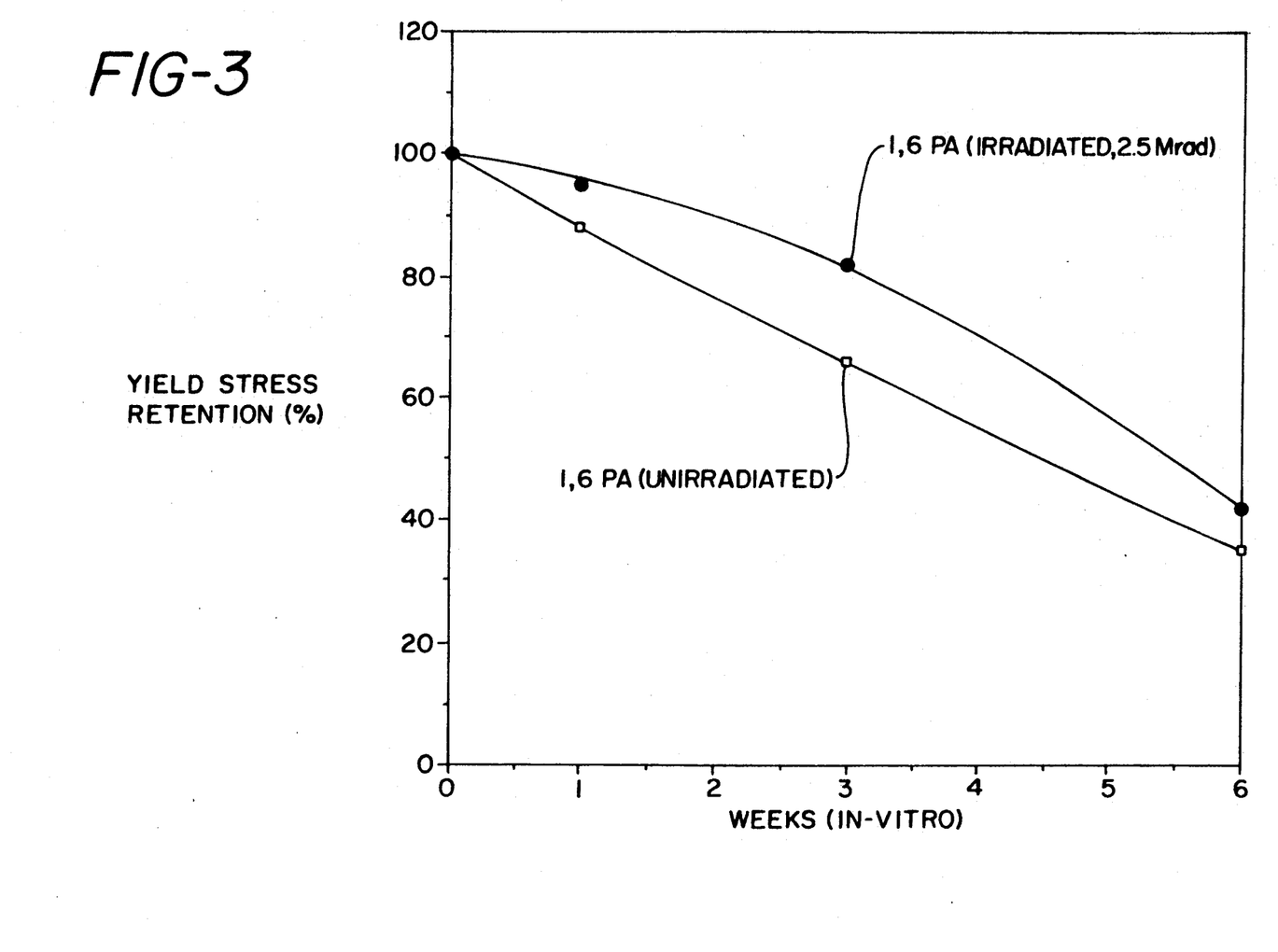
FIGS. 3 and 4 are plots of the yield stress retention in vitro over time of preferred aromatic polyanhydrides made by the improved process of this invention, before and after the polyanhydrides are subjected to irradiation.
Figure 4:
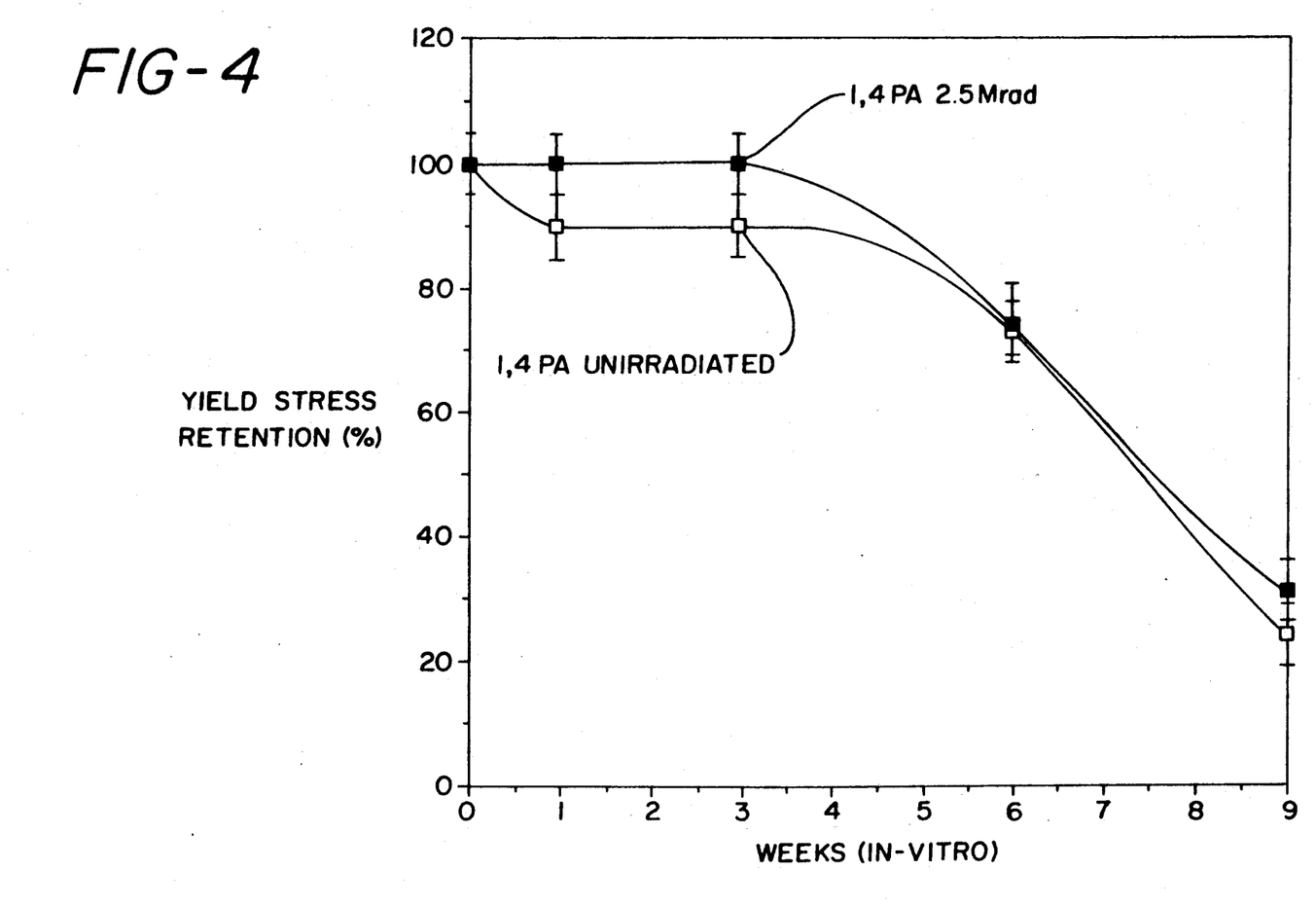

The physical properties of poly[1,6-bis(carboxyphenoxy)-hexane anhydride] and poly[1,4-bis(carboxyphenoxy)butane anhydride] made substantially in accordance with the synthesis techniques described above, where the polymerization temperature was 200° to 220° C. and the polymerization time was 200 minutes, are tabulated in Tables 2 and 3, and illustrated in FIGS. 3 and 4.

CONTROL EXAMPLE

Three step polymerization of 1,6-bis(acetoxycarboxy phenoxy)hexane via Domb and Langer method (J. Polym. Sci., 25, 3373 (1987, Macromol., 25, 12 (1992), U.S. Pat. No. 4,757,128)

The method described below is the same as Domb and Langer's method. That is, the monomer, 1,6-bis(p-carboxyphenoxy)hexane, was not recrystallized three times from NMP, but was simply washed with acetone without further purification.

The anhydride monomer was also prepared by Domb and Langer's method. That is, after refluxing for 15 minutes, the unreacted monomer/impurities were removed by filtration. The remaining acetic anhydride was removed as described by Domb and Langer.

Therefore, to a flamed-out, dry 100 ml 1-neck round bottom flask equipped with an overhead mechanical stirrer, vacuum adapter, 75° adapter, distillate bend with a vacuum take-off and a 50 ml collection flask, 33.5 grams of freshly prepared 1,6-bis(acetoxycarboxyphenoxy)hexane was added via a nitrogen purged glove box.

The assembly was then secured to a high vacuum (<10 microns) diffusion pump and placed in a high temperature oil bath at 180° C. The stirred anhydride monomer immediately began to melt. Shortly thereafter, a high volume of distillate (acetic anhydride) began to evolve, and was collected. The low viscosity melt polymerization was allowed to continue under high vacuum (10 to 30 microns) with stirring for a total reaction time of 120 minutes.

The first low molecular weight polymer, poly[1,6-bis(carboxyphenoxy)hexane anhydride], was removed from the bath, cooled to room temperature under a stream of nitrogen, isolated and ground. The polymer was the placed under vacuum at 50° C. for 24 hours. The final yield was 70 to 75 percent.

A second poly[1,6-bis(carboxyphenoxy)hexane anhydride] was also prepared and isolated by the method described above, except the polymerization temperature was 200° C. The inherent viscosities of the first and second polymers are given in Table 1 and are designated as "Experiment C".

A third poly[1,6-bis(carboxyphenoxy)hexane anhydride] was also prepared and isolated by the method described above, except the polymerization temperature was 180° C. and the polymerization time was 240 minutes.

A fourth poly[1,6-bis(carboxyphenoxy)hexane anhydride] was also prepared and isolated by the method described above, except the polymerization temperature was 200° C. The inherent viscosities of the third and fourth polymers are given in Table 1 and are designated as "Experiment D".

TABLE 1

MOLECULAR WEIGHTS OF POLY[1,6-BIS(CARBOXYPHENOXY)HEXANE ANHYDRIDE] AS A FUNCTION OF TIME (MINUTES) AT A REACTION TEMPERATURE OF 180 OR 200 C.

| | | INHERENT VISCOSITY (dl/g) AT A REACTION TIME (MIN) | | | |
| | RECRYSTALLIZATION | TEMPERATURE (180 C.) | | TEMPERATURE (200 C.) | |
| EXPERIMENT | SOLVENT | 120 | 240 | 120 | 240 |
|---|---|---|---|---|---|
| A | NMP | 0.58, 0.63, 0.72* | | 1.1 | |
| B | NMP | | 0.56, 0.60, 0.74* | | 1.31 |
| C (CONTROL)** | NONE | 0.21 | | 0.25 | |

TABLE 1-continued
MOLECULAR WEIGHTS OF POLY[1,6-BIS(CARBOXYPHENOXY)HEXANE ANHYDRIDE] AS A FUNCTION OF TIME (MINUTES) AT A REACTION TEMPERATURE OF 180 OR 200 C.

| | | INHERENT VISCOSITY (dl/g) AT A REACTION TIME (MIN) | | | |
|---|---|---|---|---|---|
| | RECRYSTALLIZATION | TEMPERATURE (180 C.) | | TEMPERATURE (200 C.) | |
| EXPERIMENT | SOLVENT | 120 | 240 | 120 | 240 |
| D (CONTROL)** | NONE | | 0.21 | | 0.32 |

*POLYMERIZATION REPEATED THREE TIMES
**NOT AN EXAMPLE OF THIS INVENTION

Table 1 summarizes the results of preparing poly(anhydride)s at 180° C. with purification of the acid by the claimed method (3 times recrystallized with NMP), and by Langer's method (washing with a non-solvent such as ether or acetone).

The results indicate that purification by recrystallization with NMP leads to higher molecular weights at a reaction temperature of 180° C. (I.V. >0.60 dl/g) than described by Domb and Langer and others in the literature. At higher reaction temperatures (200° C.) with the pure acid, the molecular weights are even higher (I.V. >1.1 dl/g).

However, purification by washing with a non-solvent (acetone/ether, i.e., Domb and Langer's method), but without recrystallization, leads to low molecular weights (0.2 to 0.3 dl/g), even at higher reaction temperatures (200° C).

Therefore, by properly purifying the acid and using higher reaction temperatures and longer reaction times, it is possible to obtain much higher molecular weights than those reported in the literature. These higher molecular weights can be obtained without the introduction of branching, crosslinking, or gelatin, as determined by solubility in low boiling solvents (chloroform), NMR, FT-IR, etc.

TABLE 2
PHYSICAL PROPERTIES OF POLY[1,6-(CARBOXYPHENOXY)HEXANE ANHYDRIDE]

| CYLINDRICAL DUMBBELLS #2428-59 | STRENGTH (PSI) | YIELD (%) ELONGATION | MODULUS (PSI) | % STRENGTH RETAINED | I.V. (dl/g) |
|---|---|---|---|---|---|
| UNANNEALED | 4537 | 9.5 | 43910 | N/A | 0.57* |
| ANNEALED** | 5630 | 7 | 75830 | N/A | 0.57* |
| ONE WEEK IN-VITRO | 4960 | 6.6 | 75540 | 88 | 0.56 |
| THREE WEEK IN-VITRO | 3740 | 5.8 | 57680 | 66 | 0.45 |
| SIX WEEK IN-VITRO | 2049 | 3.2 | 42980 | 36 | 0.32 |
| IRRADIATED (2.52 Mrad) | 5940 | 6 | 74800 | 100 | 0.60 |
| IRRADIATED, ONE WK IN-VITRO | 6220 | 8 | 77470 | 100 | 0.53 |
| IRRADIATED, THREE WK IN-VITRO | 5130 | 6.3 | 69680 | 85 | 0.45 |
| IRRADIATED, SIX WK IN-VITRO | 2515 | 3.6 | 38680 | 42 | 0.3 |

**ANNEALED 85 C./6 HRS.
*AFTER PROCESSING
N/A = NOT APPLICABLE
STANDARD DEVIATION OF 10%
DATA IS AN AVERAGE OF 8 TO 12 CYLINDRICAL DUMBBELLS

TABLE 3
PHYSICAL PROPERTIES OF POLY[1,4-BIS(CARBOXYPHENOXY)BUTANE ANHYDRIDE]

| CYLINDRICAL DUMBBELLS #2411-96 | STRENGTH (PSI) | YIELD (%) ELONGATION | MODULUS (PSI) | % STRENGTH RETAINED | YIELD* |
|---|---|---|---|---|---|
| UNANNEALED | 7400 | 11.5 | 75600 | N/A | YES |
| ONE WEEK IN-VITRO | 6300 | 9.3 | 77300 | 85 | YES |
| THREE WEEK IN-VITRO | 6700 | 9.6 | 78600 | 90 | YES |
| SIX WEEK IN-VITRO | 5400 | 8.7 | 58000 | 73 | NO |
| NINE WEEK IN-VITRO | 1800 | 3 | 52000 | 24 | NO |
| UNANNEALED, IRRADIATED (2.5 Mrad) | 6500 | 8.0 | 94000 | N/A | YES |
| IRRADIATED, ONE WK IN-VITRO | 6500 | 9.5 | 79000 | 100 | YES |
| IRRADIATED, THREE WK IN-VITRO | 6500 | 9.2 | 80000 | 100 | YES |
| IRRADIATED, SIX WK IN-VITRO | 4800 | 6 | 59000 | 74 | NO |
| IRRADIATED, NINE WK IN-VITRO | 2200 | 3.3 | 55000 | 32 | NO |

*YIELD = DID SAMPLE PHYSICALLY YIELD
N/A = NOT APPLICABLE
STANDARD DEVIATION OF 10%
DATA IS AN AVERAGE OF 8 TO 12 CYLINDRICAL DUMBBELLS

The results in Table 2, and FIG. 3 indicate that the aromatic poly(anhydride)s have high strength and appear to display a linear decrease in strength as a function of time in-vitro. Results also indicate that articles prepared from the aromatic poly(anhydride)s are cobalt sterilizable, since the strength retention at the various in-vitro time periods for unirradiated and irradiated test articles are approximately equal and as such lead to useful biomedical articles.

In-vitro results also show that the poly(anhydride)s are hydrolyzable, and therefore bioabsorbable, by the fact that a steady decrease occurs in the molecular weight in-vitro (Table 2).

Results (Table 3, FIG. 4) also indicate that different breakdown profiles can be obtained for the poly(anhydride)s depending upon the initial molecular weight of the polymer. That is, if the starting molecular weight was higher (I.V. >0.8 dl/g) initially (i.e., 1,4-polyanhydride, FIG. 4), an induction period, where little change in physical strength occurs, followed by a linear decrease in physical strength is observed. However, if the molecular weight was lower initially (i.e., 1,6-polyanhydride, FIG. 3), the initial induction period is not observed.

Figure 5:
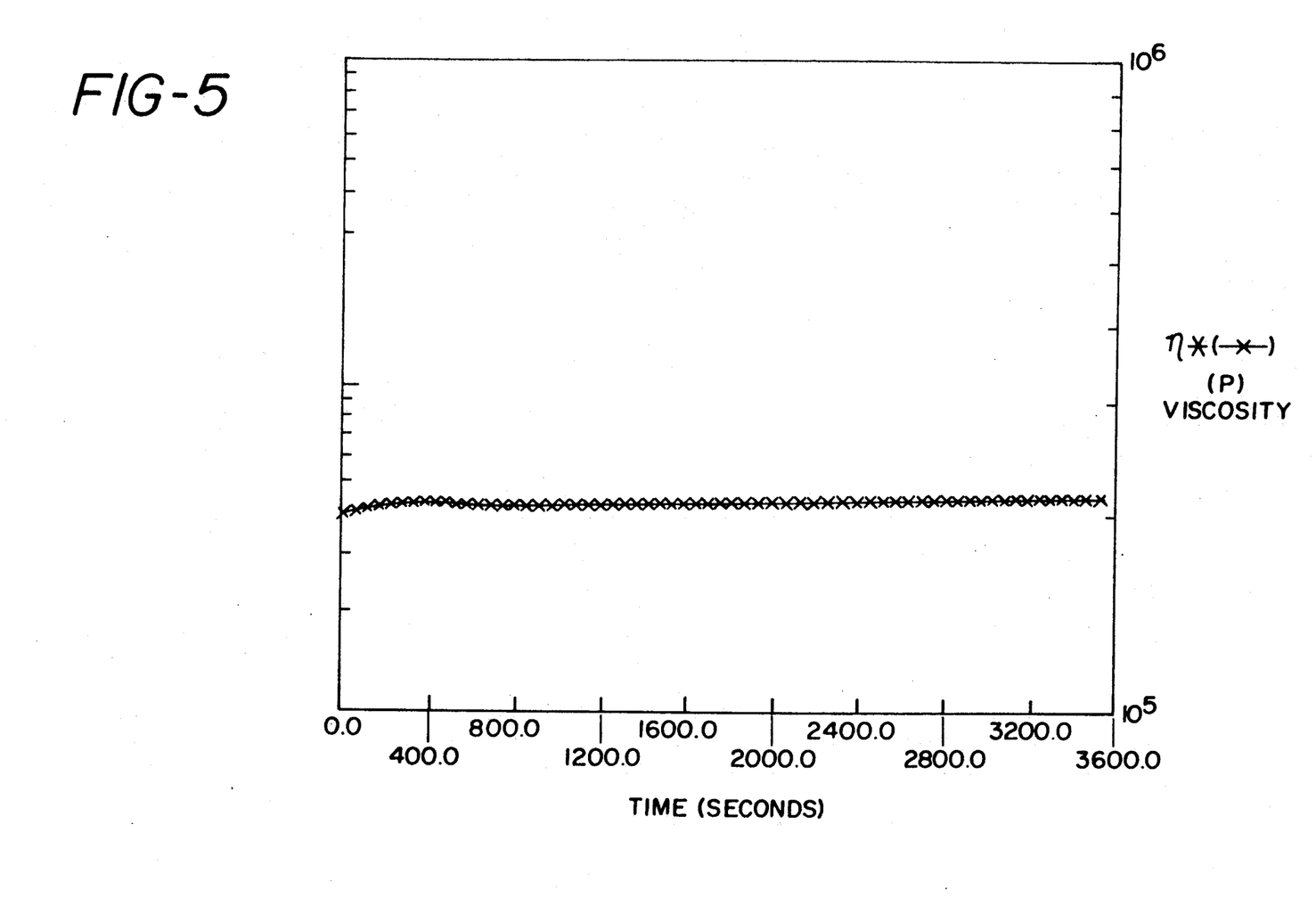
FIG. 5 is a plot of the melt viscosity of a preferred aromatic polyanhydride at 220° C. under a nitrogen atmosphere for 50 minutes.

The thermal stability results indicate that the poly(anhydride)s are melt processable and can be molded by melt processing techniques. That is, as shown in FIG. 5, essentially no change in melt viscosity occurs over a time of 50 minutes under a nitrogen atmosphere at 220° C. for a poly[1,6-bis(carboxyphenoxy)hexane anhydride] prepared as described in Example 1, experiment "A", where the polymerization time was 200 minutes and the polymerization temperature was 200° C. Results also indicate that the molded articles are dimensionally stable.

EXAMPLE 2

Copolymerization of 1,4-bis(acetoxycarboxyphenoxy)butane and 1,6-bis(acetoxycarboxyphenoxy)hexane via modified Domb and Langer method (J. Polym. Sci., 25, 3373 (1987) Macromol., 25, 12 (1992), U.S. Pat. No. 4,757,128)

To a flamed-out, dry 250 ml 1-neck round bottom flask equipped with an overhead mechanical stirrer, vacuum adapter, 75° adapter, distillate bend with a vacuum take-off and a 50 ml collection flask, 11 grams of freshly prepared 1,4-bis(acetoxycarboxyphenoxy)butane and 33 grams of 1,6-bis(acetoxycarboxyphenoxy)hexane (Example 1) were added via a nitrogen purged glove box.

The assembly was then secured to a high vacuum (<10 microns) diffusion pump and placed in a high temperature oil bath at 220° C. The stirred anhydride monomer immediately began to melt and a distillate (acetic anhydride) began to evolve, and was collected. After 15 to 20 minutes, the viscous melt was no longer stirrable under the present reactor configuration. At such time, the polymerization was allowed to continue under high vacuum (10 to 30 microns) without stirring for a total reaction time of 200 minutes.

The high molecular weight copolymer, poly[1,4bis(-carboxyphenoxy)butane anhydride-co-1,6-bis(carboxyphenoxy)hexane anhydride], was removed from the bath, cooled to room temperature under a stream of nitrogen, isolated and ground. The polymer was then placed under vacuum at 50° C. for 24 hours. The final yield was 70 to 75 percent. The molecular weight as determined by inherent viscosity was 0.83 dl/g.

EXAMPLE 3

Extrusion of aromatic polyanhydrides

In the preparation of fibers, especially surgical filaments, the polymers are melt extruded through a spinnerette in a conventional manner to form one or more filaments.

Extrusion of the polymers described herein, on a laboratory scale, was accomplished using an INSTRON Capillary Rheometer. Larger scale extrusions would require equipment such as a single screw extruder.

For example, a sample of poly(1,4-bis(carboxyphenoxy)butane anhydride], prepared in accordance with the procedures of the subject invention, an I.V. of 1.0 dl/g, was evaluated using the INSTRON Capillary Rheometer. It was packed in the preheated extrusion chamber, the temperature raised to 250° C., and melt extruded through a 40 mil die (L/D =25.2) after a dwell time of 13 minutes. A ram speed of 2cm/min. (a shear rate of 236 s$^{-1}$) was used; the apparent viscosity being 29,400 poise.

While extrusion temperatures depend on both the polymers Tm and on the melt viscosity of the material at a given temperature, extrusion of the subject polymers at temperatures of about 10° to 75° C. above the Tm is usually saftisfactory. The extrusion temperatures of the example polymers described herein ranged from 200° to 250° C. The extrudate was taken up through an ice water quench bath at 24 feet/minute, although other bath temperatures and take-up speeds occasionally were used.

The extrudate filaments (which have been allowed to crystallize sufficiently—the fibers may be annealed at elevated temperature prior to drawing) are subsequently drawn about 5× to 7.5× in a one or multistage drawing process in order to achieve molecular orientation and improve tensile properties. The manner of drawing is as follows:

The extrudate (diameter range, 18.0 to 19.5 and typically 16-20 mils) is passed through rollers at an input speed of four feet per minute and into a heated draw bath of glycerine. The temperatures of the draw bath can vary from 25° C. to about 170° C depending upon the Tg, Tm, and the crystallization characteristics of the polymer. The example described herein employed a temperature of 100° C. The draw ratio in this first stage of drawing can vary from 3× to about 7×; the example described herein employed a draw ratio of 4×.

The partially drawn fibers are then placed over a second set of rollers into a glycerine bath (second stage) kept at temperatures ranging from 50° to 190° C. The example described herein did not employ a second stage draw. Draw ratios can be applied in this second stage. The fiber was passed through a water-wash, taken up on a spool, and dried. A set of hot rollers can be substituted for a portion or all of the glycerine draw bath. The resulting oriented filaments develop good straight and knot tensile strengths.

Dimensional stability of the oriented filaments may be enhanced by subjecting the filaments to an annealing treatment. This treatment consists of heating the drawn filaments, in this example, to a temperature of from about 60° C. to about 170° C., most preferably from about 90° C. to 160° C. while restraining the filaments to control shrinkage. This process may begin with the filaments initially under tension or with up to 20% shrinkage allowed prior to restraint. The filaments are held at the annealing temperature for a few minutes to a few days or longer depending on the temperature and processing conditions. In general, annealing for up to about 24 hours is satisfactory for the polymers of the invention. Optimum annealing time and temperature for maximum fiber in-vivo strength retention and dimensional stability is readily determined by simple experimentation for each fiber composition. Other spinning conditions than those shown here can also be employed without limiting the scope of this invention.

Thus, the diameter, the straight and knot tensile strengths, Young's Modulus, and elongation at break of the monofilament prepared as set forth above, prior to annealing, are 9.6 mils, 45,500 psi, 33,600 psi, 363,000 psi, and 26%, respectively.

We claim:

1. In a process for preparing an aromatic polyanhydride by the sequential steps of:
   a) reacting an aromatic dicarboxylic acid with an anhydride so as to form an aromatic anhydride prepolymer, b) isolating and purifying the prepolymer, and
c) polymerizing the prepolymer under melt polycondensation conditions;

the improvement wherein the aromatic dicarboxylic acid is purified so that acid is at least about 99.5 weight percent pure prior to reacting said acid without anhydride.

2. The process of claim 1 wherein the acid is purified by first removing salt impurities formed from the preparation of said acid such that said acid has less than bout 0.3 weight percent of said salt impurities, and then recrystallizing the acid.

3. The process of claim 2 wherein said salt impurities are removed by repeatedly suspending said acid in a strongly acid aqueous solution.

4. The process of claim 3 wherein said acid is repeatedly recrystallized.

5. The process of claim 4 wherein the improvement further comprises conducting the polymerization of the prepolymer at a temperature no less than about 200° C.

6. The process of claim 5 wherein the improvement further comprises conducting the reaction of the acid with an excess of the anhydride at reflux for at least 60 minutes.

7. The process of claim 6 wherein each carboxyl group of said acid is attached directly to an aromatic ring.

8. The process of claim 7 wherein the reaction of the acid with the anhydride does not incorporate a coreactant at a concentration which would render the subsequently formed aromatic polyanhydride nonabsorbable.

9. The process of claim 8 wherein the reaction of the acid with the anhydride is free of any coreactant which would render the subsequently formed aromatic polyanhydride nonabsorbable.

10. The process of claim 9 wherein the reaction of the acid with the anhydride is free of any coreactant possessing an aromatic polyester functionality.

11. The process of claim 10 wherein the acid is represented by the following formula:

wherein n = 1-20, inclusive.

12. The process of claim 11 wherein is 1 to 10, inclusive.

13. The process of claim 12 wherein the anhydride is an anhydride of a monofunctional carboxylic acid.

14. The process of claim 13 wherein the anhydride is acetic anhydride.

15. An aromatic polyanhydride prepared by the process of claim 1 or 14.

16. The aromatic polyanhydride of claim 15 wherein the polyanhydride has an inherent visocisity as measured in chloroform at 25° C. no less than about 0.6 dl/g.

17. The aromatic polyanhydride of claim 16 wherein the polyanhydride has an inherent viscosity as measured in chloroform at 25° C. no less than about 1.0 dl/g.

18. The aromatic polyanhydride of claim 17 wherein the polyanhydride has a tensile strength greater than about 3000 psi.

19. The aromatic polyanhydride of claim 18 wherein the polyanhydride is melt processed so as to form a surgical device.

20. The aromatic polyanhydride of claim 19 wherein said device is a wound closure device.

21. The aromatic polyanhydride of claim 20 wherein said wound closure device is a surgical clip, staple or suture.

22. The aromatic polyanhydride of claim 19 wherein said device is an adhesion prevention barrier.

23. The aromatic polyanhydride of claim 18 wherein said device is melt or solution processed so as to form a vehicle for drug delivery.

* * * * *